United States Patent [19]

Radebaugh et al.

[11] Patent Number: 4,820,522

[45] Date of Patent: Apr. 11, 1989

[54] ORAL SUSTAINED RELEASE ACETAMINOPHEN FORMULATION AND PROCESS

[75] Inventors: Galen W. Radebaugh, Maple Glen; John L. Murtha, Holland; Robert Glinecke, Glenside, all of Pa.

[73] Assignee: McNeilab, Inc., Spring House, Pa.

[21] Appl. No.: 78,138

[22] Filed: Jul. 27, 1987

[51] Int. Cl.$^4$ .................................................. A61K 9/22
[52] U.S. Cl. .................................... 424/468; 424/469; 424/464; 424/470; 424/80
[58] Field of Search .................. 424/80, 465, 470, 473

[56] References Cited

U.S. PATENT DOCUMENTS

| | | | |
|---|---|---|---|
| 4,013,785 | 3/1977 | Weintraub et al. | 424/465 |
| 4,189,469 | 2/1980 | Gleixner et al. | 424/78 |
| 4,369,308 | 1/1983 | Trubiano | 514/960 |
| 4,439,453 | 3/1984 | Vogel | 424/470 |
| 4,661,521 | 4/1987 | Salpekar et al. | 424/465 |
| 4,702,918 | 10/1987 | Ushimaru et al. | 424/461 |

*Primary Examiner*—William R. Dixon, Jr.
*Assistant Examiner*—David M. Brunsman
*Attorney, Agent, or Firm*—Joseph J. Brindisi

[57] ABSTRACT

An acetaminophen-sustained release tablet or tablet layer is formed by making a wet granulation, using Povidone (PVP) in water or alcohol-water as the granulating fluid which is mixed with acetaminophen, hydroxyethyl cellulose, a wicking agent e.g. microcrystalline cellulose, then drying and milling the granulation and blending with dry powdered erosion promoter, e.g. pregelatinized starch, wicking agent, lubricant e.g. magnesium stearate and glidant e.g. silicon dioxide, and compressing the resultant granulation, which upon administration results in a slow release of the acetaminophen.

17 Claims, No Drawings

ORAL SUSTAINED RELEASE ACETAMINOPHEN FORMULATION AND PROCESS

This invention relates to a sustained release form of acetaminophen, and is more particularly concerned with an acetaminophen-containing matrix formed from granulations of acetaminophen mixed with inactive powered excipients plus hydroxyethyl cellulose (HEC) using an aqueous solution of Povidone U.S.P. (polyvinylpyrrolidone—PVP) as the granulated agent, which granulations are dried, milled, blended with additional inactive powdered excipients, and then compressed into a tablet, and to the process of making the acetaminophen-containing matrix in a manner so that the rate of release of acetaminophen can be varied or controlled.

BACKGROUND OF PRESENT INVENTION

Acetaminophen (APAP) is a well-known analgesic and antipyretic drug. In the United States, it is available for non-prescription over-the-counter sale in conventional liquid, suppository, capsule, tablet and caplet dosage forms. The tablet and caplet dosage forms typically contain 325 mg acetaminophen as "regular strength" or 500 mg as "extra strength". Normally, regular strength tablets or caplets are taken as one or two every four hours, and the extra strength tablets or caplets are taken as one or two every six hours. Ideally, it would be desirable to extend th dosing interval while maintaining the initial plasma concentrations achievable with conventional tablets or caplets. This would provide immediate and extended therapeutic analgesic or antipyretic effect and reduce the number of doses necessary, thereby making therapy more convenient. A way to do this has now been found, using the present invention, whereby two tablets or caplets each containing 650 mg acetaminophen can be formulated to provide both immediate release and sustained release or sustained release alone such that the dosing interval can be extended to at least eight (8) hours. In addition, the quantity (amount) of the sustained release matrix can be adjusted up or down to produce tablets for sustained release that have more or less than 650 mg of acetaminophen. For example, a tablet containing 500 mg of acetaminophen can be manufactured from the same composition by simply decreasing the size and weight of the final tablet by a multiple of 10/13. The present invention can be used to obtain any desired sustained release acetaminophen tablets of different dosages, e.g. a 500 mg sustained release tablet which results in lower blood plasma levels over eight hours, than with the 650 mg tablet, and desired longer or shorter time periods, e.g. twelve hours are possible. From a practical standpoint eight (8) hours might be the most desired interval. The matrix of the present invention can be used to make acetaminophen sustained release pharmaceutical preparations in compressed tablet form. The matrix materials used are compressed into a shaped tablet form. The term "tablet" as used herein includes tablets of any shape, and includes caplets, which are tablets having a capsule shape. The tablets may be coated with a pharmaceutically acceptable coating material or have pharmaceutically acceptable coloring added to the composition prior to compression.

PRIOR ART

Both hydroxyethyl cellulose (HEC) and polyvinyl pyrrolidone (PVP) have been used in pharmaceutical compositions, such as tablets, including sustained release compositions. However, the materials have not been used in the same way for the same purposes in a sustained release acetaminophen tablet composition. In U.S. Pat. No. 4,189,469 the examples show pharmaceutical compositions containing a xanthine as the active ingredient together with hydroxyethyl cellulose, PVP, and certain excipients. However, no wicking agent or erosion promoting agent is used there, so that the method of obtaining the sustained release affect is different in Applicant's invention. The ratio of drug to hydroxyethyl cellulose used is much higher in Applicant's sustained release formulations. Also, the reference does not refer to the use of wet granulation techniques which are required in Applicant's invention.

U.S. Pat. No. 4,264,573 teaches the use of PVP but does not teach the use of hydroxyethyl cellulose. It is typical of the many formulations for slow release via controlled surface erosion which are known in the prior art.

SUMMARY OF THE INVENTION

The present invention, in its process aspect is directed to the process of preparing an acetaminophen-sustained release shaped and compressed tablet characterized by a slow release of the acetaminophen upon administration comprising the following steps:

(A) forming a granulating agent by dissolving 5–25 parts by weight povidone in water or in an alcohol-water mixture;

(B) blending together the following ingredients in dry powder form;

| Ingredient | Parts by Weight |
| --- | --- |
| Acetaminophen | 325 |
| Hydroxyethyl Cellulose | 5–25 |
| wicking agent e.g. Microcrystalline Cellulose | 5–25 |

(C) adding the granulating agent from Step A to the blended powders from Step B, and mixing in a high shear granulator to form a wet granulation;

(D) drying the wet granulation of Step C;

(E) milling the dried granulation from Step D;

(F) thoroughly blending the milled dried granulation from Step E with the following ingredients in dry powder form;

| Ingredient | Parts by Weight |
| --- | --- |
| erosion promoter e.g. Pregelatinized Starch | 1–15 |
| wicking agent e.g. Microcrystalline Cellulose | 5–45 |
| libricant e.g. Magnesium Stearate | 0–10 |
| glidant e.g. Colloidal Silicon Dioxide | 0–5 |

(G) compressing the final granulation from Step F into a tablet or tablet layer.

In its product aspect the present invention is directed to a shaped and compressed sustained release therapeutic composition comprising acetaminophen as the therapeutically-active medicament and granulating agent and excipients combined into a matrix, characterized by a slow release of the acetaminophen medicament upon administration, wherein the graulating agent and excipients includes a combination of two polymers, hydroxyethyl cellulose and povidone, and wherein the total amount of ingredients other than acetaminophen in the sustained release matrix may, in the most preferred embodiments, be less than fifteen (15) percent of the weight of said shaped and compressed composition.

The preferred tablets of this invention include a shaped and compressed acetaminophen sustained release tablet made by wet granulating the Active & Excipients ingredients of Part I with the Granulating Agent of Part II, drying and milling the resultant granulations, and then blending with the Excipients of Part III and compressing into a tablet, wherein the ingredients of Parts I, II and III comprise the following:

|         | Ingredient | Parts by Weight |
|---------|------------|-----------------|
| Part I  | Active & Excipients | |
|         | Acetaminophen | 325 |
|         | Hydroxyethyl Cellulose | 5–25 |
|         | Microcrystalline Cellulose | 5–25 |
| Part II | Granulating Agent | |
|         | Povidone | 5–25 |
|         | Water or Alcohol-Water | q.s |
| Part III| Excipients | |
|         | Pregelatinized Starch | 2–15 |
|         | Microcrystalline Cellulose | 5–45 |
|         | Magnesium Stearate | 0–10 |
|         | Colloidal Silicon Dioxide | 0–5 |

The invention preferably is utilized in the form of a bi-layer tablet containing both an immediate release layer and a sustained release layer.

In addition to the hydroxyethyl cellulose and PVP polymers discussed above which are "Matrix Binding Agents", the commonly used excipients which are granulated with the acetaminophen must include a "wicking agent" (to wick fluids into the matrix) such as microcrystalline cellulose, and an "erosion promoter" such as pregelatinized starch. Additional excipients which are added to the granulated and dried ingredients include a wicking agent such microcrystalline cellulose, an erosion promoter such as pregelatinized starch, and optionally a lubricant such as magnesium stearate and a glidant such as colloidal silicon dioxide. The use of a lubricant is preferred, while the use of a glidant is possible but not usually needed.

DETAILED DESCRIPTION OF THE INVENTION

The acetaminophen sustained release matrix pharmaceutical tablets of the present invention are made by adding granulating agent to a dry powder blend of active drug and inactive excipients to form wet granulations, which are then dried and finely divided, e.g. by milling the dried granulations into a finer powder form, then blending with additional inactive powdered excipients and compressing into tablets. Tablets can be readily manufactured using conventional tabletting equipment.

The tablets of the present invention have novel and advantageous features. A primary advantage is that the tablets are bioerodible when swallowed, that is, no insoluble tablet shaped device remains to be excreted or removed from the body after acetaminophen is depleted from the tablet. The acetaminophen sustained release matrix uses hydroxyethyl cellulose (Hydroxyethyl Cellulose NF) and povidone (Povidone USP) (Plasdone ® K29/32) (PVP) as the Matrix Binding Agents for obtaining the sustained release effect. This combination of two well-known pharmaceutically acceptable polymers, in the relative proportions here used and in the manner used is believed to be a major novel feature of the present invention. In the most preferred embodiments of the invention, the amount of hydroxyethyl cellulose used is on the general order of four percent or less of the amount of acetaminophen, while the amount of povidone is on the general order of four percent or less of the amount of acetaminophen used. This means the acetaminophen sustained release matrix of the present invention is capable of producing dosage forms having very high drug/matrix binding agent ratios. This results in reducing the size or number of tablets needed, making the product easier to swallow, less expensive and more desirable to the consumer.

Another advantage of this invention is that the rate of matrix erosion when the tablet is swallowed can be modified so that the degree and/or length of the sustained release effect of the matrix can be easily modified by simply altering the levels of the other excipients, aside from the hydroxyethyl cellulose and the povidone (PVP). Hence, the rate at which acetaminophen is released from the tablet and subsequent absorption from the gut into the bloodstream can be modified to match the desired blood plasma concentration versus time profile.

The acetaminophen sustained release matrix of the present invention can be used alone as a shaped and compressed tablet (tablet can be any shape such as oval, round, caplet or spherical), or as part of a multi-layered tablet containing an immediate or quick-release layer to elevate the blood levels of acetaminophen quickly and also containing a sustained release portion to maintain the elevated blood level. Hence, the present invention can be used to prepare tablets with two or more layers, each with a significantly different release rate of the same component, or to prepare tablets of different components where a combination of drugs is desired.

The acetaminophen sustained release matrix, in our currently preferred embodiments, contains approximately three percent hydroxyethyl cellulose and approximately three percent povidone (PVP), with the balance consisting of various pharmaceutically acceptable, common excipients. The matrix tablets or tablet layers of the present invention have a very high drug-to-excipients ratio on the order of 85 percent acetaminophen to 15 percent excipients by weight. This results in a drug to total matrix weight ratio of approximately 1:1.2.

As discussed, the hydroxyethyl cellulose and PVP polymers are Matrix Binding Agents. The additional commonly used excipients that are granulated with the acetaminophen include a Wicking Agent (to wick fluids into the matrix) such as microcrystalline cellulose. Additional excipients that are added to the granulated and dried ingredients include a wicking agent such as microcrystalline cellulose, an Erosion Promoter such as pregelatinized starch, and a lubricant such as magnesium stearate.

For each of the ingredients used in the sustained release matrix of the present invention, aside from the acetaminophen, the hydroxyethyl cellulose, and the povidone (PVP) there exists less preferred alternative or equivalent materials which could be used in its place. The following Table I lists each of the various preferred ingredients, the purpose of the ingredient, the preferred weight of such preferred ingredient, the usable weight range of the preferred ingredient, other less preferred alternatives or equivalents which can be substituted for the preferred ingredient, the preferred weight of such alternate ingredient and the usable weight range of such alternate ingredient needed for the sustained release layer containing 325 mg of acetaminophen. For matrices (tablets or caplets) of a higher or lower level of acetaminophen, the amounts of ingredients and their ranges would be proportionately increased or decreased.

The ingredients are listed in Table I under Part I Active & Excipients, Part II Granulating Agent, Part III Excipients, since they are used in this manner in the process by which the tablets of the present invention are made.

The preferred process which is utilized from form the most preferred acetaminophen sustained release matrix of the present invention is to mix together the dry powdered active drug, acetaminophen, the dry powdered matrix binding agent, hydroxyethyl cellulose, and the dry powdered wicking agent, microcrystalline cellulose in a mixer/granulator. A granulating fluid or solution is formed by dissolving povidone into water at a ratio of 19.1 grams of povidone to 100 grams of water. The resultant granulating agent is sprayed onto the above admixed powders while they are being mixed in the mixer/granulator so as to form a wet granulation. The wet granulation thus obtained is dried and milled. At this point, a small amount of dry powdered excipients such as pregelatinized starch, microcrystalline cellulose and magnesium stearate are added, and mixed with the milled granulations, after which they are compressed thereby forming the sustained release matrix.

TABLE I

SUSTAINED RELEASE ACETAMINOPHEN MATRIX

| Preferred Ingredient | Purpose | (mg) Wt. per Tablet | (mg) Range | Alt. or Equiv. | (mg) Wt. per Tablet | (mg) Range |
|---|---|---|---|---|---|---|
| Part I - Active & Excipients | | | | | | |
| Acetaminophen, USP | Active | 325 | — | — | — | — |
| Hydroxyethyl Cellulose NF (Natrosol*/250L) | Matrix Binding Agent | 10.7 | 5-25 | — | — | — |
| Microcrystalline Cellulose NF, (Avicel* PH 101,102,103,105) | Wicking Agent | 10.7 | 5-25 | Powdered Cellulose (Solka Floc*) | 10.7 | 5-25 |
| Part II - Granulating Agent | | | | | | |
| Povidone, USP (Plasdone* K29/32) | Matrix Binding Agent | 10.7 | 5-25 | — | — | — |
| Purified Water, USP | Solvent | q.s water-alcohol (up to 50%) | | | | |
| Part III - Excipients | | | | | | |
| Microcrystalline Cellulose USP(Avicel* PH 101,103,103,105) | Wicking Agent | 15.0 | 5-45 | Powdered Cellulose (Solka Floc*) | 15.0 | 5-45 |
| Pregelatinized Starch, NF (corn, wheat, or potato source) | Erosion Promoter | 5.0 | 2-15 | Starch NF (corn, wheat or potato) or rice starch, | 5.0 | 5-10 |
| | | | | Sodium Starch Glycolate NF(Explotab*) | 3.0 | 1-10 |
| | | | | Croscarmellose Sodium NF (Ac Di Sol*) | 3.0 | 1-10 |
| | | | | Crospovidone NF(Povidone*XL) | 3.0 | 1-10 |
| Magnesium Stearate NF | Lubricant | 5.0 | 0-10 | Stearic Acid NF | 5.0 | 5-10 |

EXAMPLE I

Acetaminophen Sustained Release Bi-Layer Tablet

This example illustrates a bi-layer tablet in which there is both an immediate release layer and a sustained release layer. The immediate release layer is analogous in composition and manufacturing procedure to currently available over-the-counter acetaminophen non-sustained release tablets. It is the sustained release layer that utilizes the matrix of the present invention. The acetaminophen content of the entire tablet is 650 mg.

The bi-layer tablet uses the following ingredients:

| Ingredient | mg/Tablet |
|---|---|
| A. Immediate Release Layer | |
| Part I - Active and Excipients | |
| Acetaminophen, USP | 325.0 mg |
| Powdered Cellulose, NF | 42.3 mg |
| Pre-gelatinized Starch, NF | 16.0 mg |
| Part II - Granulating Agent | |
| Starch, NF | 26.0 mg |
| Purified Water USP | q.s. |
| Part III - Excipients | |
| Sodium Laurel Sulphate, NF | 0.75 mg |
| Magnesium Stearate, NF | 2.0 mg |
| Total | 412.05 mg |
| B. Sustained Release Layer | |
| Part I - Active and Excipients | |
| Acetaminophen, USP | 325.0 mg |

-continued

| Ingredient | mg/Tablet |
|---|---|
| Hydroxyethyl Cellulose, NF (Natrosol* 250L) | 10.7 mg |
| Microcrystalline Cellulose, NF (Avicel* PH 101) | 10.7 mg |
| Part II - Granulating Agent | |
| Povidone, USP (Plasdone* K29/32) | 10.7 mg |
| Purified Water, USP | q.s. |
| Part III - Excipients | |
| Microcrystalline Cellulose, USP (Avicel* PH 101) | 15.0 mg |
| Pregelatinized Starch, NF (Starch 1500)* | 5.0 mg |
| Magnesium Stearate, NF | 5.0 mg |
| Total | 382.1 mg |
| Total Tablet Weight | 794.15 mg |

The above ingredients are utilized to make a bi-layer tablet, by the following working directions:

Working Directions

A. Immediate Release Layer
  1. Weigh the components of Part I and add them to the bowl of a fluid bed granulator (Aeoromatic).
  2. Prepare the granulating agent (Part II) by adding the Purified Water to a processing tank (approximately 15 grams water for each gram of Starch NF). Slowly mix in the starch and heat the mixture until the temperature reaches 82° C.-84° C.
  3. With the components of Part I in a heated fluidized state (inlet air temperature 75° C. to 85° C.), spray the granulating agent onto the powders.
  4. After all the granulating agent has been sprayed, dry the granulated powders to a moisture content of 1.4–1.9% as determined by loss on drying (e.g. Computrac).
  5. Sieve the dried granulation (e.g. Glatt Quick Sieve: Stator No. 3, Screen No. 1.5 mm, 1000 RPM). Other machines such as Fitzpatrick Communition Mill can be used.
  6. Blend the sieved and dried granulation with the powders of Part III using a suitable mixer such as a twin-shell, ribbon or planetary mixer.

B. Sustained Release Layer
  1. Weigh the components of Part I and preblend in a high shear mixer (Fielder: impeller speed of approximately 250 RPM for 1 minute).
  2. Prepare the granulating agent (Part II) by dissolving the Povidone USP in th Purified Water USP (a ratio of 19.1 grams of povidone to 100 gm of water).
  3. Spray the granulating agent at a rate of 400 ml/min onto Part I in the high shear mixer. Granulate the mixture for one minute after the addition of Part II (Fielder: impeller speed of approximately 3000 RPM).
  4. Remove the completed wet granulation from the high shear mixer and load it into the product bowl of a fluid bed apparatus (e.g. Aeromatic or Glatt). With an inlet air temperature of approximately 60° C., dry the granulation to a moisture level of 2.0 to 2.5% as determined by loss on drying (e.g. Computrac). The wet granulation can also be dried on trays in drying ovens.
  5. Sieve the dried granulation (Glatt Quick Sieve: 1.5 mm Screen, Stator No. 3, 395 RPM). Other machines such as a Fitzpatrick Communition Mill can be used.
  6. Blend the sieved and dried granulation with the powders of Part III using a suitable mixer such as a twin-shell, ribbon or planetary mixer.

C. Compression of Tablets or Caplets
  1. Load the granulation of the immediate release layer into one hopper and the granulation of the sustained release layer into the second hopper of a bi-layer tableting machine (e.g. Stokes Versapress). Compress tablets using 0.749×0.281×0.060 extra deep concave capsule shaped tooling (Tablet Tooling of other shapes such as oval or round can also be used). The sustained release layer has a target weight of 382.1 mg and the immediate release layer has a target weight of 412.05 mg. Ideal tablet hardness immediately after compression is 7–12 Kp.

The bi-layer tablets of Example I were tested in twelve adult male human subjects and compared to non-sustained release (immediate release only) tablets in a cross-over design. Two tablets of Example I, which contained 1300 mg of acetaminophen, were dosed at time=0 hour. The non-sustained release tablets, each containing 500 mg acetaminophen were dosed as two tablets (1000 mg acetaminophen) also at time=0 hour. Subjects were fasted at least 8 hours prior to administration of the dose. Blood samples were taken from each subject at 0, 1, 1.5, 2, 3, 4, 6, 8, 10 and 12 hours. Plasma was separated from the blood and the concentration of acetaminophen in each sample was determined. The results are shown numerically in Tables 2a and 2b. The results show that two bi-layer tablets of Example I, when compared to two tablets of non-sustained release acetaminophen (1000 mg dose), achieve the following: comparable rate of absorption: comparable maximum plasma concentration; and comparable extent of absorption (AUC or area under the curve) when adjusted for dose. Theoretically, the 1300 mg dose should provide 130% of the AUC of the 1000 mg dose. The results from Tables 2a and 2b show comparable extents of absorption by the following calculation: (64.3 mcg/ml divided by 49.5 mcg/ml)×100%=130%.

The tablets of Example I provide the opportunity to dose 30% more acetaminophen in a more convenient manner by extending the dosing interval to at least eight hours.

TABLE 2a

Sustained Release Acetaminophen 650 mg bi-layer tablets. (Example I) Average Plasma Concentration Levels of Acetaminophen (mcg/ml) in twelve subjects after administration of two tablets (1300 mg). Average AUC equaled 64.3 mcg/hr.

| TIME (HOURS) POST DOSING | | | | | | | | | |
|---|---|---|---|---|---|---|---|---|---|
| 0 | 1.0 | 1.5 | 2.0 | 3.0 | 4.0 | 6.0 | 8.0 | 10.0 | 12.0 |
| Average (mcg/ml) | | | | | | | | | |
| 0 | 12.5 | 12.8 | 11.9 | 10.0 | 7.5 | 4.4 | 2.6 | 1.6 | 1.0 |

TABLE 2b

Non-sustained Release Acetaminophen 500 mg tablets. Average Plasma Concentration Levels of Acetaminophen (mcg/ml) in twelve subject. Average AUC equaled 49.5 mcg/hr.

| TIME (HOURS) POST DOSING | | | | | | | | | |
|---|---|---|---|---|---|---|---|---|---|
| 0 | 1.0 | 1.5 | 2.0 | 3.0 | 4.0 | 6.0 | 8.0 | 10.0 | 12.0 |
| Average (mcg/ml) | | | | | | | | | |

TABLE 2b-continued

Non-sustained Release Acetaminophen 500 mg tablets. Average Plasma Concentration Levels of Acetaminophen (mcg/ml) in twelve subject. Average AUC equaled 49.5 mcg/hr.

| TIME (HOURS) POST DOSING | | | | | | | | | |
|---|---|---|---|---|---|---|---|---|---|
| 0 | 1.0 | 1.5 | 2.0 | 3.0 | 4.0 | 6.0 | 8.0 | 10.0 | 12.0 |
| 0 | 12.1 | 11.4 | 10.0 | 7.3 | 5.3 | 2.9 | 1.8 | 1.1 | 0.6 |

EXAMPLE II

Acetaminophen Sustained Release Tablet Containing 650 mg of Acetaminophen in Matrix Form This example illustrates an all-matrix (mono-layer) tablet in which there is only a sustained release layer. The working directions are analogous to the working directions for the sustained release layer described in Example I except that the amounts of all ingredients are proportionally increased such that the final tablet contains 650 mg acetaminophen. Tablets can be compressed using capsule, oval, round or other appropriately shaped tooling. The final target weight of the compressed tablet is 764.2 mg.

| Ingredient | mg/Tablet |
|---|---|
| Part I - Active and Excipients | |
| Acetaminophen, USP | 650.0 mg |
| Hydroxyethyl Cellulose, NF (Natrosol* 250L) | 21.4 mg |
| Microcrystalline Cellulose, NF (Avicel* PH 101) | 21.4 mg |
| Part II - Granulating Agent | |
| Povidone, USP (Plasdone* K29/32) | 21.4 mg |
| Purified Water, USP | q.s |
| Part III - Excipients | |
| Microcrystalline Cellulose, NF (Avicel* PH 101) | 30.0 mg |
| Pregelatinized Starch, NF (Starch 1500*) | 10.0 mg |
| Magnesium Stearate, NF | 10.0 mg |
| Total | 764.2 mg |

EXAMPLE III

Acetaminophen Sustained Release Bi-layer Tablet Containing More than a total of 650 mg acetaminophen This example illustrates a bi-layer tablet which is analogous to the tablet described in Example I, except all amounts of ingredients per tablet and final weight of the tablet are proportionally increased. The amount of the increase is theoretically indefinite, but one practical amount would be a 16⅔ mg increase in the amount of acetaminophen such that the total amount of acetaminophen in a tablet would be 666⅔ mg. Hence, if the tablets were dosed as two every eight hours, the maximum total amount of acetaminophen consumed in a 24 hours period would be 4 grams. The working directions for the immediate release layer and the sustained release layer are analogous to the working directions described in Example I. Tablets can be compressed using capsule, oval, round or other appropriately shaped tooling. For a tablet containing a total of 666.66 mg (an approximation of 666⅔ mg) acetaminophen, the sustained release layer has a target weight of 391.99 mg and the immediate release layer has a target weight of 422.65 mg.

| Ingredient | mg/Tablet |
|---|---|
| A. Immediate Release Layer | |
| Part I - Active and Excipients | |
| Acetaminophen, USP | 333.33 mg |
| Powdered Cellulose, NF | 43.4 mg |
| Pregelatinized Starch, NF | 16.4 mg |
| Part II - Granulating Agent | |
| Starch, NF | 26.7 mg |
| Purified Water, USP | q.s. |
| Part III - Excipients | |
| Sodium Laurel Sulfate, NF | 0.77 mg |
| Magnesium Stearate, NF | 2.05 mg |
| Total | 422.65 mg |
| B. Sustained Release Layer | |
| Part I - Active and Excipients | |
| Acetaminophen, USP | 333.33 mg |
| Hydroxyethyl Cellulose, NF (Natrosol* 250L) | 11.0 mg |
| Microcrystalline Cellulose, NF (Avicel* PH 101) | 11.0 mg |
| Part II - Granulating Agent | |
| Povidone, USP (Plasdone* K29/32) | 11.0 mg |
| Purified Water, USP | q.s. |
| Part III - Excipients | |
| Microcrystalline Cellulose, NF (Avicel* PH 101) | 15.4 mg |
| Pregelatinized Starch, NF (Starch 1500*) | 5.13 mg |
| Magnesium Stearate, NF | 5.13 mg |
| Total | 391.94 mg |
| Total Tablet Weight | 814.64 mg |

EXAMPLE IV

Acetaminophen Sustained Release Bi-layer Tablet Containing Less Than a Total of 650 mg Acetaminophen This example illustrates a bi-layer tablet which is analogous to the tablet described in Example I, except all amounts of ingredients per tablet and final weight of the tablet are proportionally decreased. One practical decrease in the amount of acetaminophen would be 150 mg such that the total amount of acetaminophen in a tablet would be 500 mg. The working directions for the immediate release layer and the sustained release layer are analogous to the working directions described in Example I. Tablets can be compressed using capsule, oval, round or other appropriately shaped tooling. For a tablet containing a total of 500 mg acetaminophen, the sustained release layer has a target weight of 293.89 mg and the immediate release layer has a target weight of 316.92 mg.

| Ingredient | mg/Tablet |
|---|---|
| A. Immediate Release Layer | |
| Part I - Active and Excipients | |
| Acetaminophen, USP | 250 mg |
| Powdered Cellulose, NF | 32.5 mg |
| Pregelatinized Starch, NF | 12.3 mg |
| Part II - Granulating Agent | |
| Starch, NF | 20.0 mg |
| Purified Water, USP | q.s |
| Part III - Excipients | |
| Sodium Laurel Sulfate, NF | 0.58 mg |
| Magnesium Stearate, NF | 1.54 mg |
| Total | 316.92 mg |
| B. Sustained Release Layer | |
| Part I - Active and Excipients | |

-continued

| Ingredient | mg/Tablet |
|---|---|
| Acetaminophen, USP | 250.0 mg |
| Hydroxyethyl Cellulose, NF (Natrosol* 250L) | 8.23 mg |
| Microcrystalline Cellulose, NF (Avicel* PH 101) | 8.23 mg |
| Part II - Granulating Agent | |
| Povidone, USP (Plasdone* K29/32) | 8.23 mg |
| Purified Water, USP | q.s |
| Part III - Excipients | |
| Microcrystalline Cellulose, NF (Avicel* PH 101) | 11.5 mg |
| Pregelatinized Starch, NF (Starch 1500*) | 3.85 mg |
| Magnesium Stearate, NF | 3.85 mg |
| Total | 293.89 mg |
| Total Tablet Weight | 610.81 mg |

What is claimed is:

1. The process of preparing an acetaminophen-sustained release shaped and compressed tablet characterized by a slow release of the acetaminophen upon administration comprising the following steps:
   (A) forming a granulating agent by dissolving 5-25 parts by weight of the total composition of Povidone in water or in an alcohol-water mixture;
   (B) blending together the following parts by weight of the total composition of ingredients with sufficient acetaminophen to comprise 68 to 94 percent by weight of the total composition in dry powder form;

| Ingredient | Parts by Weight |
|---|---|
| Hydroxyethyl Cellulose | 5-25 |
| wicking agent | 5-25 |

(C) adding the granulating agent from Step A to the blended powders from Step B, and mixing in a high shear granulator to form a wet granulation;
   (D) drying the wet granulation of Step C;
   (E) milling the dried granulation from Step D;
   (F) thoroughly blending the milled dried granulation from Step E with the following parts by weight of the total composition of ingredients in dry powder form:

| Ingredient | Parts by Weight |
|---|---|
| erosion promoter | 1-15 |
| wicking agent | 5-45 |
| lubricant | 0-10 |
| glidant | 0-5; and |

(G) compressing the final granulation from Step F into a tablet or tablet layer.

2. The process of claim 1 wherein:
   in Step A, when any alcohol is used, it is Alcohol USP or Dehydrated Alcohol USP or Methyl Alcohol USP or Isopropyl Alcohol USP, and is used in a quantity equal to or less than the water in the alcohol-water mixture;
   in Step B the wicking agent used is Microcrystalline Cellulose or Powdered Cellulose;
   in Step F the erosion promoter used is 2-15 parts by weight of either Pregelatinized Starch or Starch NF or rice starch, or is 1-10 Parts by Weight of Sodium Starch Glycolate or Croscarmellose Sodium or Crospovidone; the lubricant used is Magnesium Stearate or Stearic Acid; and, the Glidant used is Colloidal Silicon Dioxide or Fumed Silicon Dioxide.

3. The process of claim 2 wherein:
   in Step A water is used;
   in Step B the wicking agent used is Microcrystalline Cellulose; in Step F the erosion promoter used is Pregelatinized Starch; and the lubricant used is Magnesium Stearate.

4. The process of claim 3 wherein the specific ingredients and amounts used are:

| Step | Ingredient | Parts by Weight |
|---|---|---|
| A | water | q.s |
|   | Povidone | 10.7 |
| B | Acetaminophen | 325.0 |
|   | Hydroxyethyl Cellulose | 10.7 |
| F | Pregelatinized Starch | 5.0 |
|   | Microcrystalline Cellulose | 15.0 |
|   | Magnesium Stearate | 5.0 |

5. The process of claim 4 wherein the Parts by Weight shown refer to milligrams per tablet.

6. A shaped and compressed sustained release therapeutic composition comprising Acetaminophen, a granulating agent and excipients combined into a matrix, characterized by a slow release of the Acetaminophen upon administration, wherein the granulating agent and excipients include Hydroxyethyl Cellulose and Povidone, and wherein the total amount of granulating agent and excipients is effective to bind the Acetaminophen in a sustained release solid matrix but is less than about 35 percent of the weight of said shaped and compressed composition.

7. A shaped and compressed Acetaminophen sustained release tablet made by wet granulating a sufficient amount of Acetaminophen to comprise from about 68 to 94 percent of the total composition with the Excipients of Part I and the Granulating Agent of Part II, drying and milling the resultant granulations, and then blending with the Excipients of Part III and compressing into a tablet, wherein the ingredients of Parts I, II and III comprise the following:

|  | Ingredient | Parts by Weight |
|---|---|---|
| Part I | Excipients | |
|  | Hydroxyethyl Cellulose | 5-25 |
|  | Microcrystalline Cellulose | 5-25 |
| Part II | Granulating Agent | |
|  | Povidone | 5-25 |
|  | Water or Alcohol-Water | q.s |
| Part III | Excipients | |
|  | Pregelatinized Starch | 2-15 |
|  | Microcrystalline Cellulose | 5-45 |
|  | Magnesium Stearate | 0-10 |
|  | Colloidal Silicon Dioxide | 0-5 |

8. The tablet of claim 7 wherein the Parts by Weight refer to milligrams per tablet, and wherein the ingredients are present either in the weights indicated or in such weights multiplied by an appropriate fraction.

9. A composition according to claim 6 wherein the total amount of granulating agent and excipients is greater than about 6 but less than 15 percent of the total weight of said shaped and compressed composition.

10. A process of preparing an acetaminophen sustained release bi-layer tablet comprising a first layer of immediate release and a second layer of sustained slow release of acetaminophen according to the steps of:
  (A) preparing an immediate release layer comprising acetaminophen and pharmaceutically acceptable excipients; and
  (B) preparing a sustained release layer comprising acetaminophen as the active ingredient according to the steps of:
    (1) forming a granulating agent by dissolving about 5–25 parts by weight of the total sustained release layer of Povidone in alcohol or an alcohol-water mixture;
    (2) blending together a sufficient amount of acetaminophen to comprise 68 to 94 percent of the total weight of the sustained release layer with the following ingredients in dry powder form in parts by weight of the total sustained release layer as indicated:

| Ingredient | Parts by Weight |
|---|---|
| hydroxyethyl cellulose | 5–25 |
| wicking agent | 5–25; |

(3) adding the granulating agent from Step 1 to the blended powders from Step 2, and forming a wet granulation;
    (4) drying the wet granulation of Step 3;
    (5) milling the dried granulation Step 4;
    (6) thoroughly blending the milled dried granulation from Step 5 with the following ingredients in dry powder form;

| Ingredient | Parts by Weight |
|---|---|
| erosion promoter | 1–15 |
| wicking agent | 5–45 |
| lubricant | 0–10 |
| glidant | 0–5; and |

(C) combining and compressing the immediate release layer of Step A with the sustained release layer of Step B into a bi-layered tablet.

11. The process of claim 10 wherein:
in Step 1 the alcohol is alcohol USP, dehydrated alcohol USP, methyl alcohol USP or isopropyl alcohol USP; in Step 2 the wicking agent is microcrystalline cellulose or powdered cellulose; and
in Step 6 the erosion promoter is 2–15 parts by weight of the total sustained release layer and is either pregelatinized starch NF or rice starch, or is 1–10 parts by weight of the total sustained release layer and is sodium starch glycolate, croscarmellose sodium or crospovidone, the lubricant is magnesium stearate or stearic acid and the glidant is colloidal silicon dioxide or fumed silicon dioxide.

12. The process of claim 11 wherein:
in Step 1 the alcohol is alcohol USP;
in Step 2 the wicking agent is microcrystalline cellulose;
in Step 3 the wet granulation is formed by mixing in a high shear granulator; and
in Step 6 the erosion promoter is pregelatinized starch, the lubricant is magnesium stearate, and the glidant is colloidal silicon dioxide.

13. The process of claim 10 wherein the immediate release layer comprises a composition of the following ingredients:
  acetaminophen; powdered cellulose; starch; pregelatinized starch; sodium laurel sulphate; and a granulating agent.

14. A shaped and compressed bi-layer therapeutic composition comprising acetaminophen in a first immediate release layer and a second sustained release layer wherein the immediate release layer comprises acetaminophen and pharmaceutically acceptable excipients and the sustained release layer comprises acetaminophen, a granulating agent and excipients combined into a matrix, wherein the granulating agent and excipients of the sustained release layer include hydroxyethyl cellulose and povidone, and wherein the total amount of said granulating agent and excipients is effective to bind the acetaminophen in a sustained release solid matrix but is less than about 32 percent of the weight of the sustained release layer of said shaped and compressed bi-layer composition.

15. The therapeutic composition of claim 14 wherein the immediate release layer comprises acetaminophen; powdered cellulose; starch; pre-gelatinized starch; sodium laurel sulphate; and a granulating agent.

16. The therapeutic composition of claim 14 wherein the amount of granulating agent and excipients is greater than about 6 percent but less than about 15 percent of the total weight of the sustained release layer of said shaped and compressed bi-layer composition.

17. A shaped and compressed bi-layered immediate release layer and sustained release layer acetaminophen tablet made by combining an immediate release layer comprising acetaminophen and pharmaceutically acceptable excipients with a sustained release layer made by wet granulating a sufficient amount of acetaminophen to comprise 68 to 94 percent of the total weight of the sustained relase layer with the Excipients of Part I and the Granulating Agent of Part II, drying and milling the resultant granulations, and then blending with the Excipients of Part III and compressing the two layers into a tablet, wherein the ingredients of Parts I, II and III comprise the following:

| Ingredient | | Range of Parts by Weight of the Total Sustained Release Layer |
|---|---|---|
| Part I | Excipients | |
| | Hydroxyethyl Cellulose | 5–25 |
| | Microcrystalline Cellulose | 5–25 |
| Part II | Granulating Agent | |
| | Povidone | 5–25 |
| | Alcohol or Alcohol-Water | q.s. |
| Part III | Excipients | |
| | Pregelatinized Starch | 2–15 |
| | Microcrystalline Cellulose | 5–45 |
| | Magnesium Stearate | 0–10 |
| | Colloidal Silicon Dioxide | 0–5 |

* * * * *

UNITED STATES PATENT AND TRADEMARK OFFICE
CERTIFICATE OF CORRECTION

PATENT NO. : 4,820,522

DATED : April 11, 1989

INVENTOR(S) : Galen W. Radebaugh, John L. Murtha and Robert Glinecke

It is certified that error appears in the above-identified patent and that said Letters Patent is hereby corrected as shown below:

Delete claims 1-9

Signed and Sealed this

Twelfth Day of December, 1989

*Attest:*

JEFFREY M. SAMUELS

*Attesting Officer*  Acting Commissioner of Patents and Trademarks